United States Patent [19]

Burke et al.

[11] Patent Number: 4,865,840

[45] Date of Patent: Sep. 12, 1989

[54] TOPICAL COMPOSITIONS CONTAINING SELENOAMINO ACIDS FOR THE PREVENTION OF ULTRAVIOLET RADIATION-INDUCED SKIN DAMAGE

[76] Inventors: Karen E. Burke, 515 E. 89th St., New York, N.Y. 10028; Luis C. Calvo, 8 Avon Pl., Bayshore, N.Y. 11708

[21] Appl. No.: 44,058

[22] Filed: Apr. 29, 1987

[51] Int. Cl.⁴ ............................ A61K 7/40; A61K 7/42
[52] U.S. Cl. ...................................... 424/59; 514/937; 514/938
[58] Field of Search ....................................... 424/59, 60

[56] References Cited

PUBLICATIONS

The New England Journal of Medicine, vol. 264, SELENIUM SULFIDE INTOXICATION, Captain James W. Ransone et al., 2/23/61, 384–385.
J. Invest Dermatol, vol. 24, TOXICITY-STUDIES ON SELENIUM DISULFIDE SUSPENSION, Edward M. Shapiro, M.D. et al., (1955), 423–428.
Southern Medical J., vol. 55, EFFECT OF SELENIUM DISULFIDE ON RABBIT EYES, J. William Rosenthal et al., 1962, p. 318.
J. American Medical Association, vol. 156, USE OF SELENIUM SULFIDE SHAMPOO IN SEBORRHEIC DERMATITIS, Eugene S. Bereston, M.D., 1246–1247.
J. of Investigative Dermatology, LACK OF TOXICITY OF SELENIUM SULFIDE SUSPENSION FOR HAIR ROOTS, H. C. Maguire, Jr. et al., 8/4/62, 469–470.
Acta. path. microbiol. immunol. scand. Sect. A, vol. 91, BRIEF REPORT ORAL SELENIUM INHIBITS SKIN REACTIONS TO UV LIGHT IN HAIRLESS MICE, E. B. Thorling et al., 1983, 81–83.
Cancer Letters, vol. 27, SELENIUM INHIBITS UV-LIGHT-INDUCED SKIN CARCINOGENESIS IN HAIRLESS MICE, K. Overvad et al., 1985, 163–170.
Newsline, NUTRITIONAL SUPPLEMENTS OF SELENIUM TESTED FOR CANCER PREVENTION.
Nutrition and Cancer, PLASMA SELENIUM AND SKIN NEOPLASMS: A CASE-CONTROL STUDY, L. C. Clark et al., 1984, 13–21, vol. 6, No. 1.
Chem. Abst., 1970, vol. 80, p. 119314x, Passwater.
Chem. Abs., 1973, vol. 84, p. 31387v, Tamba.
Chem. Abs., 1980, vol. 95, p. 25566p, Ringdahl.
Chem. Abs., 1976, vol. 85, p. 177932m, Cymerman et al.

*Primary Examiner*—Dale R. Ore
*Attorney, Agent, or Firm*—Brumbaugh, Graves, Donohue & Raymond

[57] ABSTRACT

Topical application of selenoamino acids, such as L-selenomethionine, leads to significantly enhanced levels of selenium in the skin, and also to enhanced levels of selenium in the plasma and liver without toxicity. These enhanced levels of selenium provide protection from ultraviolet radiation-induced skin damage, and significantly reduce the incidence of skin cancers following ultraviolet light exposure.

15 Claims, 3 Drawing Sheets

TOPICAL COMPOSITIONS CONTAINING SELENOAMINO ACIDS FOR THE PREVENTION OF ULTRAVIOLET RADIATION-INDUCED SKIN DAMAGE

BACKGROUND OF THE INVENTION

This invention relates to compositions containing L-selenomethionine and the other selenoamino acids in a topical carrier for prevention of ultraviolet (hereinafter "UV") radiation-induced skin damage, and to a method of preventing such skin damage using selenoamino acids. The invention further relates to a method for preferentially increasing the selenium concentration in selected parts of the skin such that ultraviolet radiation-induced skin damage is reduced.

Experimental studies have been reported which suggest that the trace element selenium may prevent cancers in animals. Ip et al., 4 *Cancer Research* 31 (1981); Schrauzer, 5 *Bioinorganic Chemistry* 275 (1976); Jansson et al., 91 *Adv. Exc. Med. Biol.* 305 (1977). In addition, state by state studies of mortality rates in the United States and various foreign countries show an inverse correlation between low soil selenium levels and human cancer mortality rates. Schrauzer et al., 7 *Bioinorganic Chemistry* 23 (1977); Shamberger et al., 2 *Crit. Rev. Clin. Lab. Sci.* 211 (1971).

Retrospective analyses have established that human patients with low plasma selenium levels are more likely to develop skin cancer than patients with high plasma selenium levels. Clark et al. 6 *Nutrition and Cancer* 13 (1984). These analyses took into account other important causes of skin cancer, such as excess exposure to sunlight, arsenic and ionizing radiation, but relied on the natural occurrence of selenium from the patients' diets. Subsequent prospective studies are currently in progress to evaluate the prophylactic efficacy of dietary selenium supplements, such as selenium enriched Brewer's yeast, in patients with marked sun exposure and a recent history of skin cancer, but results are not yet available.

Two studies have been conducted in mice, evaluating the effect of oral administration of sodium selenite on the carcinogenic potential of UV light in hairless mice. Thorling et al. 91 *Acta Path. Microbiol. Immunol. Scand. Sect. A* 81 (1983); Overrad et al. 27 *Cancer Letters* 163 (1985). Those studies showed that oral administration of sodium selenite rendered the mice more resistant to the acute and sub-acute effects of UV radiation, i.e inflammation and pigmentation, and also that oral administration of selenium mediated a dose-dependent selenium protection against UV-induced skin cancer. Unfortunately, the oral doses used in these studies resulted in a moderate inhibition of animal growth rate, as reflected in the decreased weight gain of the selenium-treated mice relative to the controls.

Selenium has been incorporated in topically applied shampoos or lotions for the treatment of seborrheic dermatitis and tinea versicoler. For this application, selenium sulfide is used at levels of 1.0-2.5%. Selenium sulfide applied topically does not penetrate the skin to give increased levels of selenium in the serum or liver.

SUMMARY OF THE INVENTION

It has now been found that topical application of selenoamino acids, and particularly sulfur containing selenoamino acids such as L-selenomethionine leads to significantly enhanced levels of selenium in the skin, and also to enhanced levels of selenium in the plasma and liver without toxicity. These enhanced levels of selenium, both in the skin and in the plasma and liver provide protection from ultraviolet radiation-induced skin damage and significantly reduce the incidence of skin cancers following exposure to ultraviolet radiation.

According to the invention, selenoamino acids such as L-selenomethionine are preferably incorporated into a lotion or cream type carrier to produce a composition for application to the skin. For example, known oil-in-water emulsions used as face and hand cream bases may be advantageously employed. L-selenomethionine is preferably incorporated in the carrier at a concentration of at least 0.002%. This lower limit is selected to achieve a composition in which a reasonable amount of lotion or cream is required to provide a therapeutic amount of the selenoamino acid. Of course, if more frequent applications or larger quantities of the composition are acceptable, lower concentrations might be used. The upper limit of selenium concentration is selected to avoid acute toxic effects.

DETAILED DESCRIPTION OF THE INVENTION

Figure 1:
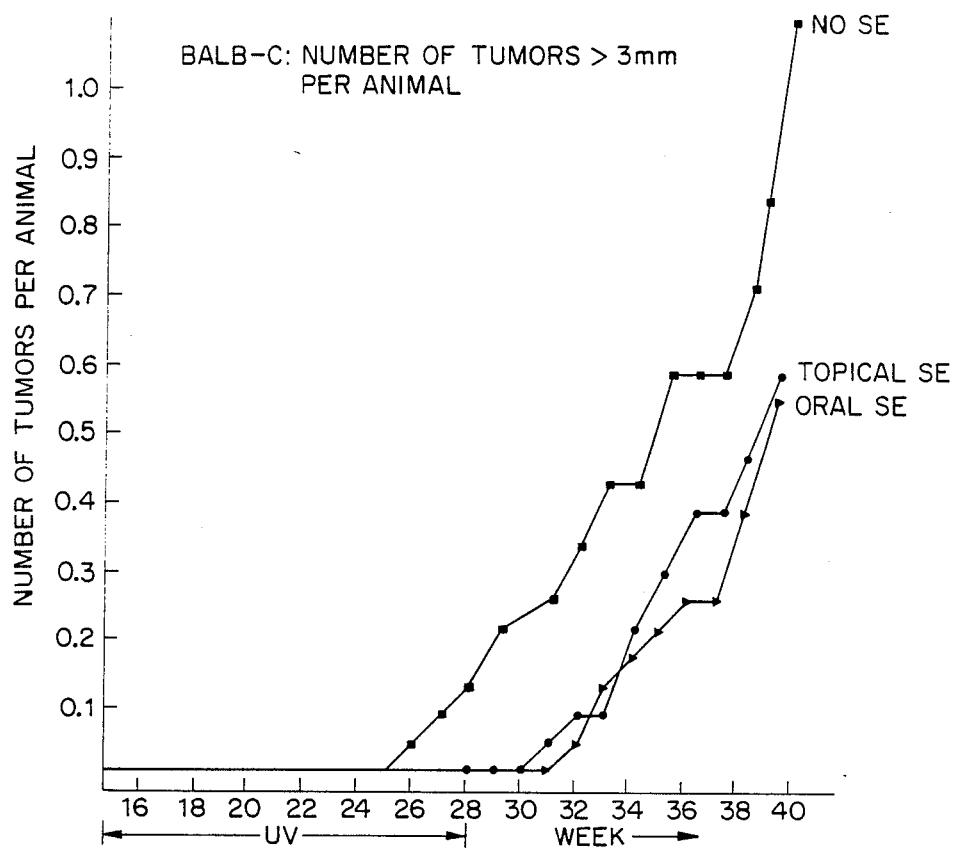
FIG. 1 graphically illustrates the effect of selenium in reducing skin cancers in UV irradiated BALB-C mice.

Topical application of selenoamino acid compositions in accordance with the invention provides a different type of protection than that afforded by conventional sunscreens, such as those containing p-amino benzoic acid, because the selenium is actually absorbed into treated human skin within a period of less than fifteen minutes. Thus, unlike a superficial sunscreen, the protective effect of the selenomethionine is not washed off by, e.g., swimming or sweating. Thus, frequent reapplication is not required to maintain protection, as is the case with known sunscreen products.

Selenoamino acid compositions according to the invention can be prepared in any suitable carrier. For example, suitable carriers are those which actually penetrate the skin and include oil-in-water emulsions of polypropylene glycol-3-myristyl ether, squalane, other unsaturated oils and branched hydrocarbons, liquid fatty acid esters, unsaturated liquid fatty alcohols and unsaturated vegetable oils formulated as hydrophilic lotions or creams. Thus the carrier may also include humectants such as glycerine or propylene glycol and other conventional additives.

Compositions containing L-selenomethionine are preferably applied daily during periods of significant exposure to UV-radiation, although this frequency may be changed in view of the concentration of selenium applied, the extent of sun exposure and damage, skin type and age. The resultant selenium concentration in the skin in the area of application is higher than that attained using a comparable oral dosage of selenium, while the levels of selenium in the untreated skin, the serum and the liver are comparable to those in animal receiving oral doses of selenium. As a result, selenoamino acids can be applied to selected regions of the skin to provide preferentially enhanced selenium levels in the localized area of application.

EXAMPLE

To determine the effectiveness of selenium supplementation in the form of topical application and oral administration of L-selenomethionine in providing protection for ultraviolet radiation-induced skin damage, 120 BALB-C female mice and 40 female Skh:2 hairless, pigmented, dark-eyed mice were obtained and separated into treatment groups as follows:

| Group | # of Animals | UV | Treatment |
|---|---|---|---|
| 1 | 30 BALB-C | + | carrier |
| 2 | 30 BALB-C | + | 0.02% L-selenomethionine lotion |
| 3 | 30 BALB-C | + | carrier + 1.5 ppm L-selenomethionine in drinking water |
| 4 | 8 BALB-C | − | carrier |
| 5 | 8 BALB-C | − | 0.02% L-selenomethionine lotion |
| 6 | 8 BALB-C | − | carrier + 1.5 ppm L-selenomethionine in drinking water |
| 7 | 12 Skh:2 | + | carrier |
| 8 | 12 Skh:2 | + | 0.02% L-selenomethionine lotion |
| 9 | 12 Skh:2 | + | carrier +1.5 ppm L-selenomethionine in drinking water |
| 10 | 4 Skh:2 | − | carrier |
| 11 | 6 BALB-C | − | L-selenomethionine soap (wash 3 time/week) |

During the treatment, the BALB-C mice were shaved on the back one per week. 100 λ of a composition according to the invention in the form of an oil-in-water emulsion location containing 0.02% L-selenomethionine was applied three times a week to the backs and ears of the mice for a period of one week prior to beginning irradiation with ultraviolet light. The lotion carrier was formulated from an oil phase containing 2½% polypropylene glycol-3-myristyl ether, 2% squalane, 0.5% safflower oil, 1% Myrj 52S emulsifier, 0.75% cetyl alcohol, 0.3% SPAN-60, 6.5% Amercol L101, 0.5% Lanocerin, 1% glyceral monostearate, 0.1% preservative, 1% Silicone 200, 1% stearic acid, and 0.5% isostearic acid; and an aqueous phase containing 68.5% distilled water, 0.75% triethanolamine, 5% propylene glycol, 0.3% preservative, 0.1% allantoin, 0.4% Germal II dissolved in 2% water, and 5% of Carbopol 941 (2.5% solution). Each 100 λ application of the composition penetrated the skin within a period of ten minutes. The composition continued to be applied thirty minutes before each thrice weekly irradiation.

Maintenance exposure times for the BALB-C mice was 50 minutes, while for the Skh:2 mice it was 15 minutes. Irradiation with four Westinghouse FS40 sunlamps was begun at 5 minute exposures, however, and increased by 5 minutes per session for the BALB-C mice and by 2.5 minutes per session for the Skh:2 mice until the respective maintenance exposure level for each type of mouse was reached. The maintenance dose of UV radiation for the BALB-C mice was 0.58 Joules/sq. cm./exposure and for the Skh:2 mice, 0.24 Joules/s. cm./exposure. This irradiation was continued for 28 weeks for the BALB-C mice (about 41 joules/sq. cm. total) and 24 weeks for the Skh:2 mice (about 15 joules/sq. cm. total). This dosage of UV irradiation has been shown to induce skin cancers in these breeds of mice.

To evaluate the effectiveness of the selenium supplementation in protecting against skin cancers and the relative merits of the claimed composition, the total number of clinically detectable skin cancers in each group was counted. These results are shown in FIGS. 1–6.

Figure 2:
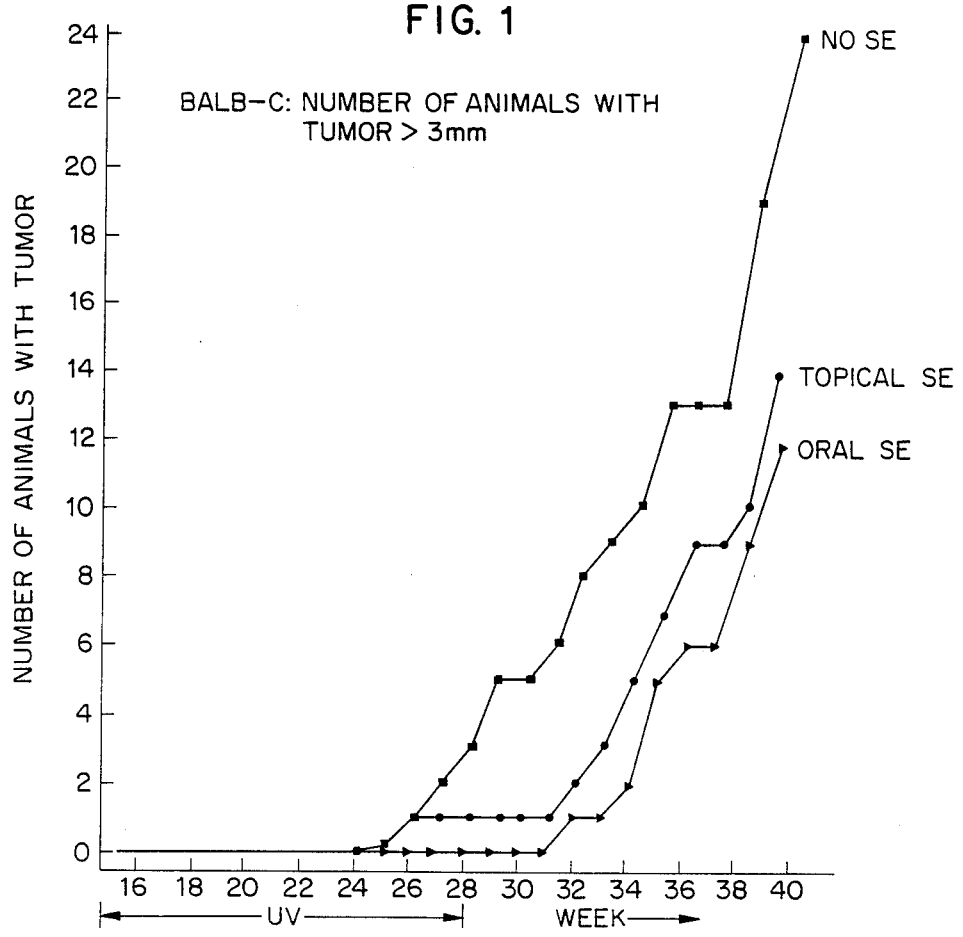
FIG. 2 graphically illustrates the effect of selenium in reducing skin cancers in UV irradiated BALB-C mice.
Figure 3:
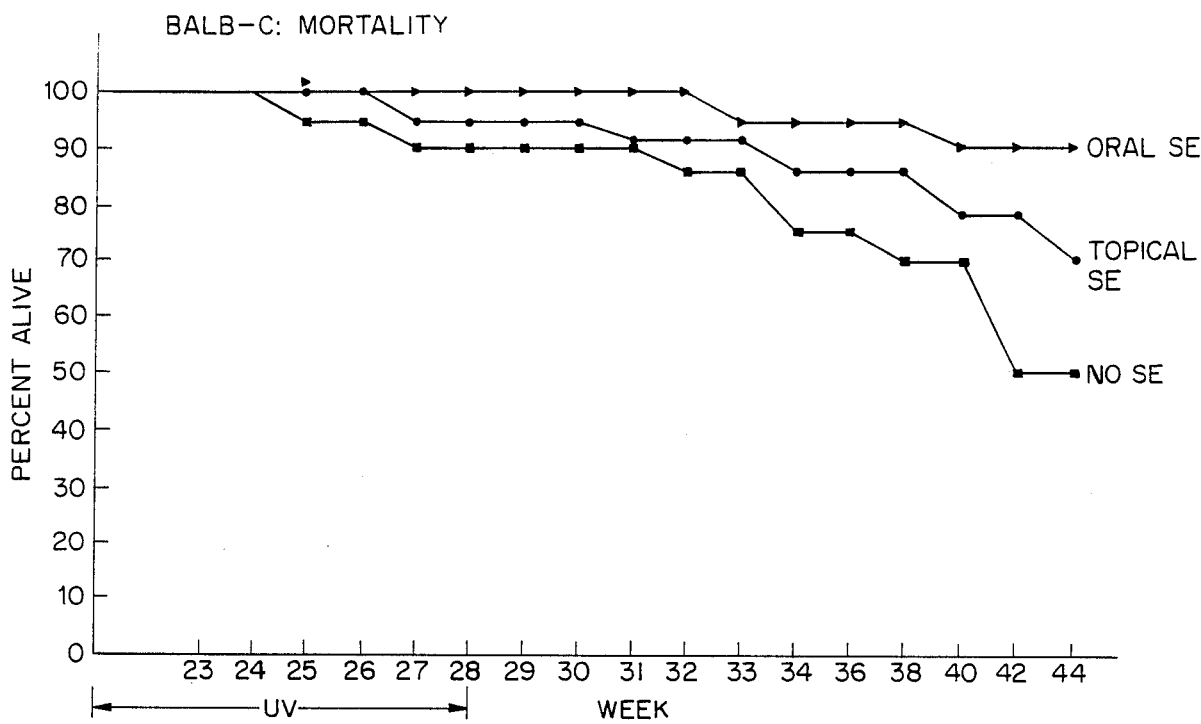
FIG. 3 graphically illustrates the effect of selenium on the mortality rate of UV irradiated BALB-C mice.

FIG. 1 shows the number of tumors over 3 mm in size observed in the three irradiated groups of BALB-C mice (Groups 1–3). FIG. 2 shows the number of animals having tumors over 3 mm in size. These figures clearly show that both topical and oral selenium supplementation lead to comparable protection against skin cancers. Tumors greater than 5 mm in size were also considered, but the observed results were inconclusive due to the complicating effect of mortality in irradiated/non-selenium supplemented mice. FIG. 3 shows the mortality rate for groups 1–3. This figure shows a clear reduction in UV-induced mortality in the selenium supplemented mice. The unirradiated control groups (groups 4–6) had no tumors observed during the experimental period, and none died during the test period.

Figure 4:
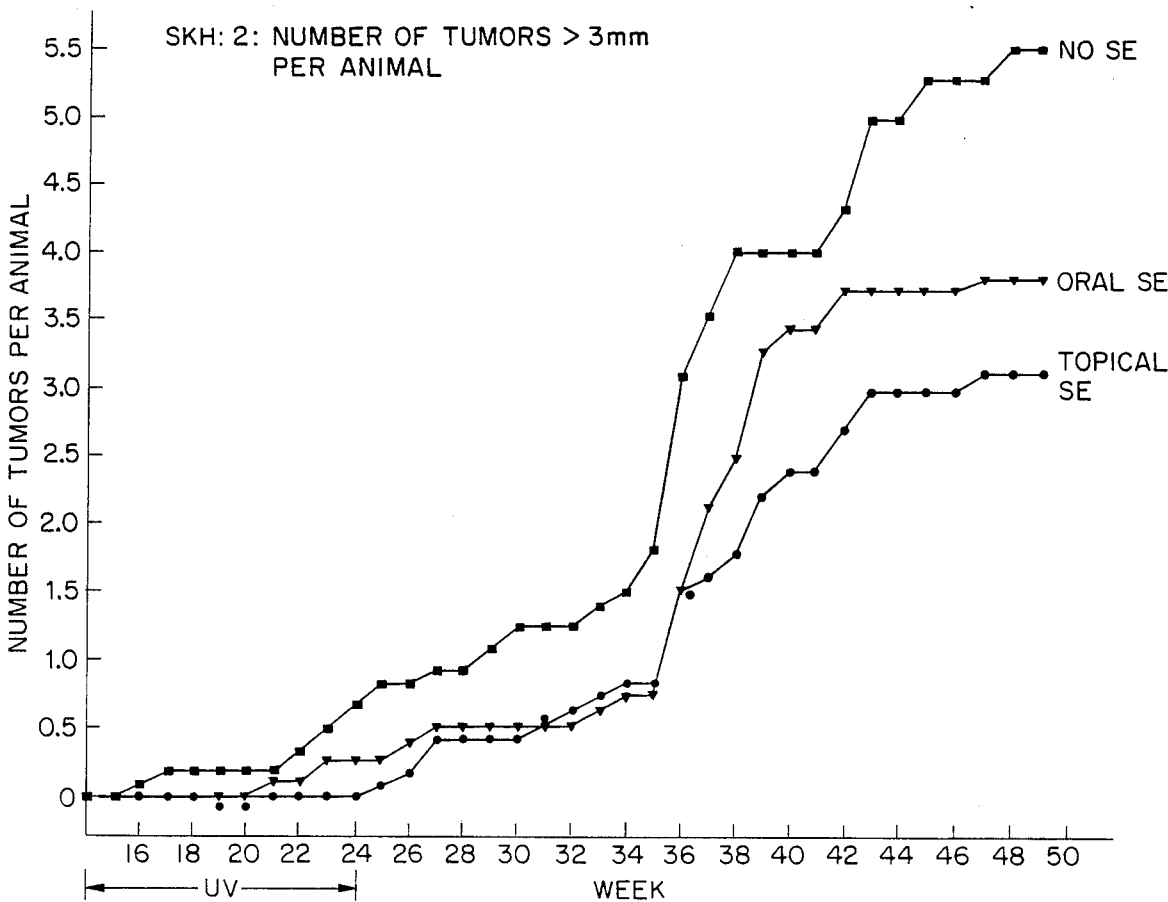
FIG. 4 graphically illustrates the effect of selenium in reducing skin cancers in UV irradiated Skh:2 mice.
Figure 5:
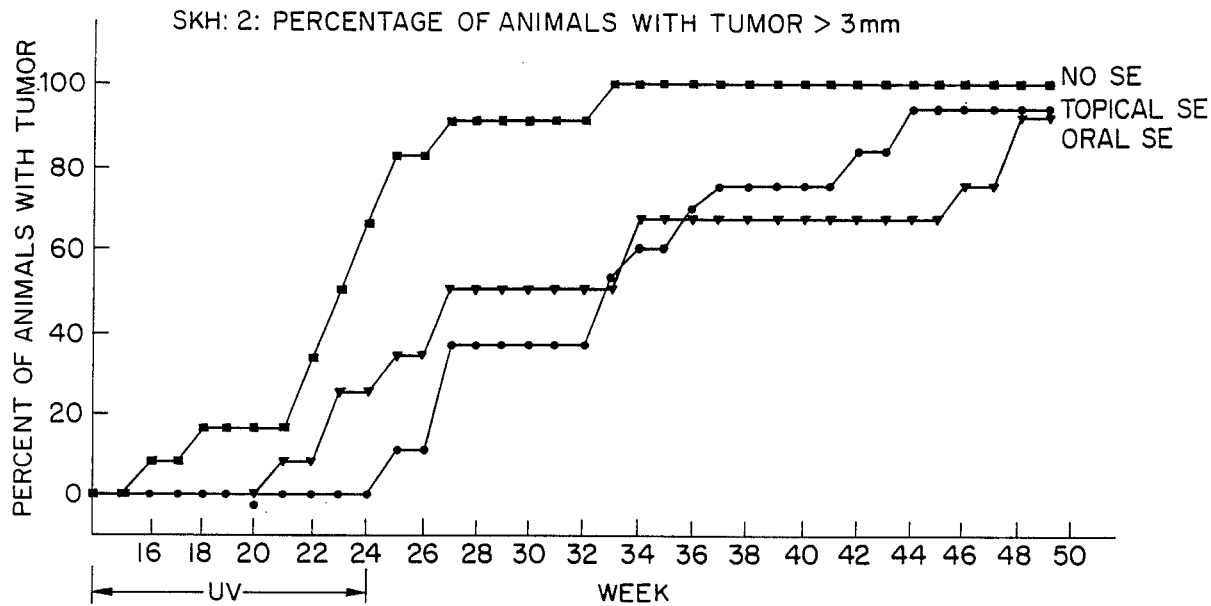
FIG. 5 graphically illustrates the effect of selenium in reducing skin cancers in UV irradiated Skh:2 mice.
Figure 6:
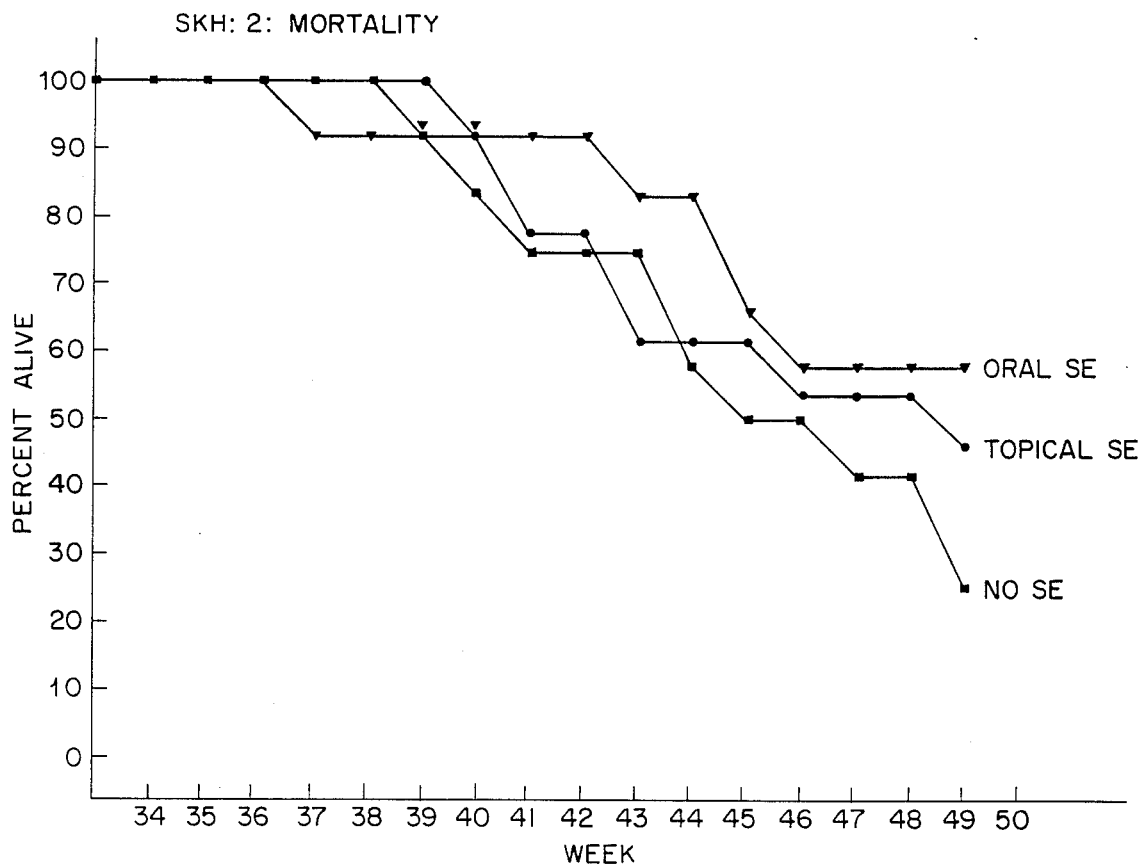
FIG. 6 graphically illustrates the effect of selenium on the mortality rate of UV irradiated Skh:2 mice.

FIG. 4 shows the number of tumors over 3 mm in size observed in the three irradiated groups of Skh:2 mice (Groups 7–9). FIG. 5 shows the numbers of animals having tumors over 3 mm in size. These figures clearly show that topical selenium application using the selenium composition and oral selenium administration lead to comparable protection against skin cancers. The observations based upon 5 mm tumors were also superior in the selenium-supplemented mice, although in this case irradiated control mortality is also a complicating factor. FIG. 6 shows the mortality rate for groups 7–9. The unirradiated control group (group 10) had no tumors observed during the experimental period, and none died during the test period.

Throughout the studies, the weights of the mice and the total feed and water intake were monitored. As shown in the analysis of the data after fifteen weeks in Tables 1 and 2, both oral and topical selenium supplementation have little effect on the feeding habits of the mice, and both treated and untreated mice were thriving.

After 12 weeks, 6 irradiated and 4 non-irradiated BALB-C mice were sacrificed, and at 39 weeks the remaining BALB-C mice were sacrificed. The liver and skin selenium levels were determined. The results of these measurements are shown in Tables 3 and 4. Clearly, topical application of the L-selenomethionine composition using the lotion carrier led to substantially enhanced selenium levels in the treated skin, and to a preferential increase in selenium levels in the localized part of the skin actually treated. Selenium-containing-soap-treated animals did not exhibit comparable levels of selenium absorption.

Since selenium is a co-factor for a free-radical quenching enzyme, glutathione peroxidase, the level of two hepatic free-radical quenching enzymes, selenium dependent glutathione peroxidase and superoxide dismutase were also tested. The results of these tests are shown in Table 5. Although an increase in selenium dependent glutathione peroxidase which might have been expected was not observed, these results, along with studies on alkaline phosphatase clearly show that there was no evidence of toxicity in the selenium treated mice.

In addition to the observed reduction of skin cancers, the topical application of the L-selenomethionine composition was observed to protect the skin against less severe types of ultraviolet radiation-induced damage such as inflammation i.e. sunburn and pigmentation.

This is illustrated in Table 6, where the pigmentation of selenium supplemented mice is reduced.

While not intending to be bound to any specific theory, it is believed that the effectiveness of the selenomethionine composition as opposed to selenium sulfide results from the solubility and absorbability of the selenomethionine. Accordingly, it is expected that other selenoamino acids such as selenocysteine and selenodiglutathione might be similarly effective.

TABLE 1

Mouse performance to 15 weeks - Burke study (GFC analysis)
(effects of mouse strain and Se-supplements in UV-exposed mice)

| TRT | Strain | UV | Se-supplement[1] | n[2] | Body Weight[3] g/mouse | Feed Intake[4] g/mouse | Water Intake[4] g/mouse |
|---|---|---|---|---|---|---|---|
| 1 | BALBC | + | none | 4 | $21.2 \pm 0.1^5$ | $434.5 \pm 3.2^5$ | $391.2 \pm 16^5$ |
| 2 | BALBC | + | topical | 4 | $22.7 \pm 0.2$ | $442.7 \pm 7.0$ | $375.2 \pm 16.4$ |
| 3 | BALBC | + | drinking water | 4 | $21.6 \pm 0.4$ | $464.4 \pm 21.8$ | $453.4 \pm 14.8$ |
| 7 | KH$_2$ | + | none | 2 | $33.1 \pm 3.8$ | $563.6 \pm 66.1$ | $531.4 \pm 85.4$ |
| 8 | KH$_2$ | + | topical | 2 | $29.6 \pm 1.3$ | $496.5 \pm 31.1$ | $594.6 \pm 43.0$ |
| 9 | KH$_2$ | + | drinking water | 2 | $28.8 \pm 0.5$ | $502.1 \pm 8.3$ | $595.2 \pm 30.7$ |
| | | | ANOVA, P values: | | | | |
| effect: | Strain | | | | $<.001$ | .002 | $<.001$ |
| | Se-supplement | | | | NS | NS | NS |
| | Strain * Se-supplement | | | | NS | NS | NS |

[1] in addition to intake of Se from the diet (0.171 ppm)
[2] replicate group of 5-7 mice each
[3] determined at 15 weeks
[4] cummulative, 4-15 weeks
[5] mean ± SEM

TABLE 2

Mouse performance to 15 weeks - Burke study (GFC analysis)
(effects of UV and Se-supplements on BALBC mice)

| TRT | Strain | UV | Supplement[5] | n[1] | Body Weight[2] g/mouse | Feed Intake[3] g/mouse | Water Intake[3] g/mouse |
|---|---|---|---|---|---|---|---|
| 1 | BALBC | + | none | 4 | $21.2 \pm 0.1^4$ | $434.5 \pm 3.2^4$ | $391.2 \pm 1.6^4$ |
| 2 | " | + | topical | 4 | $22.7 \pm 0.2$ | $442.4 \pm 7.0$ | $375.2 \pm 16.4$ |
| 3 | " | + | drinking water | 4 | $21.6 \pm 0.4$ | $464.4 \pm 21.8$ | $453.4 \pm 14.8$ |
| 4 | " | − | none | 2 | $24.3 \pm 0.3$ | $426.8 \pm 18.3$ | $385.0 \pm 15.0$ |
| 5 | " | − | topical | 2 | $24.8 \pm 0.3$ | $423.5 \pm 1.0$ | $400.0 \pm 7.5$ |
| 6 | " | − | drinking water | 2 | $22.5 \pm 1.0$ | $399.8 \pm 12.3$ | $458.2 \pm 58.2$ |
| | | | ANOVA, P values: | | | | |
| effect: | Strain | | | | $<.001$ | .030 | NS |
| | UV | | | | .013 | NS | .046 |
| | UV * Se-supplement | | | | NS | NS | NS |

[1] replicate group of 6 mice each
[2] determined at 15 weeks
[3] cummulative, 4-15 weeks
[4] mean ± SEM
[5] in addition to intake of Se from the diet (0.171 ppm)

TABLE 3

Effect of UV exposure and several modes of Se-supplementation in on tissue Se and liver glutathione peroxidase activity in BALBC mice after 3 months.

| treatment | | | tissue Se, g/g | | | liver SeGSHpx |
|---|---|---|---|---|---|---|
| UV | Supplemental Se[3] | n | dorsal skin | ventral skin | liver | nmoles NADPH/min/mg |
| + | none | 6 | $.312 \pm .027^1$ | $.336 \pm .035$ | $1.044 \pm .056$ | $122.06 \pm 7.34$ |
| | topical | 6 | $4.519 \pm .568^2$ | $1.864 \pm .193^2$ | $2.244 \pm .353^2$ | $124.15 \pm 10.51$ |
| | drinking water | 6 | $.913 \pm .074^2$ | $.728 \pm .028^2$ | $1.597 \pm .186^2$ | $125.69 \pm 14.59$ |
| − | none | 4 | $.350 \pm .034$ | $.338 \pm .037$ | $.982 \pm .043$ | $133.72 \pm 4.57$ |
| | topical | 4 | $3.886 \pm 1.219^2$ | $1.315 \pm .095^2$ | $1.939 \pm .184^2$ | $160.18 \pm 17.36$ |
| | drinking water | 4 | $.578 \pm .061^2$ | $.666 \pm .046^2$ | $1.721 \pm .112^2$ | $141.49 \pm 18.71$ |
| | soap | 4 | $.417 \pm .051$ | $.413 \pm .064$ | $.839 \pm .069$ | $140.52 \pm 19.25$ |
| | | | ANOVA results (soap data excluded), P values: | | | |
| Source | | | | | | |
| UV | | | .225 | .652 | .059 | |
| Supplemental Se | | | $<.001$ | $<.001$ | .559 | |
| Skin source | | | $<.001$ | — | — | |
| UV*Supplemental Se | | | .480 | .619 | .620 | |
| UV*Skin source | | | .798 | — | — | |
| Supplemental Se*Skin source | | | $<.001$ | | | |

TABLE 3-continued

Effect of UV exposure and several modes of Se-supplementation in on tissue Se and liver glutathione peroxidase activity in BALBC mice after 3 months.

| treatment | | | tissue Se, g/g | | | liver SeGSHpx |
|---|---|---|---|---|---|---|
| UV | Supplemental Se[3] | n | dorsal skin | ventral skin | liver | nmoles NADPH/min/mg |
| UV*Skin source*Supplemental Se | | | | .955 | | |

[1] mean ± SEM
[2] significantly different from control within UV-treatment group and column, $P < .05$.
[3] all mice fed a commercial diet which contained 0.171 ppm Se.

TABLE 4

Effects of UV exposure and two modes of Se supplementation of BALBc mice on tissue Se contents at termination of the experiment (39 weeks).

| treatment | | | Liver Se | dorsal skin Se | Ventral skin Se |
|---|---|---|---|---|---|
| UV | Se | n | ppm | ppm | ppm |
| + | none[1] | | $1.117 \pm .065^{ab}$ | $.478 \pm .115^a$ | $.333 \pm .029^a$ |
| | topical | | $1.417 \pm .150^{bc}$ | $2.007 \pm .190^b$ | $.843 \pm .076^c$ |
| | d-water | | $1.560 \pm .084^c$ | $.562 \pm .040^a$ | $.508 \pm .026^b$ |
| − | none | | $1.027 \pm .075^a$ | $.629 \pm .126^a$ | $.345 \pm .017^a$ |
| | topical | | $1.481 \pm .156^c$ | $2.255 \pm .582^b$ | $.777 \pm .069^c$ |
| | d-water | | $1.674 \pm .137^c$ | $.432 \pm .023^a$ | $.521 \pm .018^b$ |

$p < .05$
[1] all mice were fed a diet containing a nutritionally adequate amount (0.171 ppm) of Se

TABLE 5

Effects of UV exposure and two modes of Se supplementation of BALBc mice on hepatic activities of Se-dependent glutathione peroxidase (SeGSHpx) and superoxide dismutase (SOD) after 39 weeks.

| treatment | | | SeGSHpx nmoles | SOD | protein |
|---|---|---|---|---|---|
| UV | Se | n | NADPH/mg-min | EU[1]/g | mg/g |
| + | none[2] | 11 | $115.46 \pm 14.75$ | $175 \pm 52$ | $15.33 \pm .70$ |
| | topical | 13 | $85.97 \pm 9.92$ | $181 \pm 51$ | $15.45 \pm .45$ |
| | d.water | 20 | $114.91 \pm 12.20$ | $243 \pm 67$ | $15.82 \pm .41$ |
| − | none | 3 | $89.57 \pm 33.52$ | $108 \pm 12$ | $13.10 \pm .82$ |
| | topical | 4 | $83.30 \pm 20.83$ | $88 \pm 34$ | $13.96 \pm .87$ |
| | d.water | 4 | $57.98 \pm 10.82$ | $109 \pm 43$ | $16.29 \pm .86$ |
| ANOVA results, P values: | | | | | |
| source | | | | | |
| UV | | | .070 | .169 | .094 |
| Se supplement | | | .675 | .987 | .067 |
| UV * Se supplement | | | .356 | .924 | .200 |

[1] SOD was measured by the inihibition of the spontaneous oxidation of epinephrine at pH 10.2; 1 EU = 50% inhibition.
[2] All mice were fed a diet containing a nutritionally adequate amount (0.171 ppm) of Se.

TABLE 6

Pigmentation of Skh:2 Mice after Exposure to UV-Irradiation

| Week | none | Selenium topical | oral |
|---|---|---|---|
| 7 | 3.3 | 2.3 | 1.7 |
| 12 | 3.5 | 2.7 | 2.5 |
| 16 | 3.6 | 2.6 | 2.6 |

+4 = dark pigmentation
0 = no pigmentation

We claim:

1. A composition for protection from ultraviolet radiation-induced skin damage comprising an amount of a selenoamino acid effective to retard ultraviolet radiation-induced skin damage in a lotion or cream carrier suitable for topical application.

2. A composition according to claim 1, wherein the selenoamino acid is a sulfur-containing selenoamino acid.

3. A composition according to claim 2, wherein the selenoamino acid is L-selenomethionine.

4. A composition according to claim 1, wherein the carrier is an oil-in-water emulsion.

5. A composition according to claim 1, wherein the L-selenomethionine is present in an amount of at least about 0.002%.

6. A method of protecting skin from ultraviolet radiation-induced damage comprising topically applying to the skin an amount of a selenoamino acid effective to provide protection from ultraviolet radiation-induced skin damage.

7. A method according to claim 6, wherein the selenoamino acid is a sulfur-containing selenoamino acid.

8. A method according to claim 7, wherein the selenoamino acid is L-selenomethionine.

9. A method according to claim 6, wherein the L-selenomethionine is applied in an oil-in-water emulsion carrier.

10. A method according to claim 9, wherein the L-selenomethionine is present in the carrier in a concentration of at least about 0.002%.

11. A method for locally increasing the level of selenium in a selected part of the skin comprising topically applying to the selected part of the skin an amount of a selenoamino acid sufficient to locally increase the level of selenium in the skin.

12. A method according to claim 11, wherein the selenoamino acid is a sulfur-containing selenoamino acid.

13. A method according to claim 12, wherein the selenoamino acid is L-selenomethionine.

14. A method according to claim 11, wherein the L-selenomethionine is applied in an oil-in-water emulsion carrier.

15. A method according to claim 14, wherein the L-selenomethionine is present in the carrier in a concentration of at least about 0.002%.

* * * * *